United States Patent [19]

Johnson

[11] 4,196,283

[45] Apr. 1, 1980

[54] PROSTAGLANDIN DERIVATIVES

[75] Inventor: Roy A. Johnson, Kalamazoo, Mich.

[73] Assignee: The Upjohn Company, Kalamazoo, Mich.

[21] Appl. No.: 932,962

[22] Filed: Aug. 11, 1978

Related U.S. Application Data

[60] Division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.² .......................................... C07D 311/02
[52] U.S. Cl. .................................... 542/426; 260/345.2
[58] Field of Search ....................... 260/345.2; 542/426

[56] References Cited
PUBLICATIONS

Pace-Asciak et al., Biochem., 10, 3657 (1971).
Pace-Asciak et al., JACS, 98, 2348 (1976).

Primary Examiner—Nicky Chan
Attorney, Agent, or Firm—Robert A. Armitage; Morris L. Nielsen

[57] ABSTRACT

Prostaglandin ($PG_1$) derivatives having (1) a 5-keto feature, for example

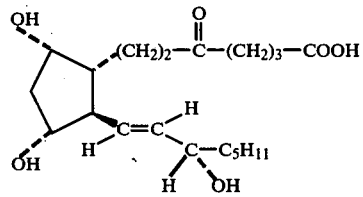

or (2) a 9-deoxy-5,9-epoxy feature together with a 4-halo or 5-hydroxy feature, for example

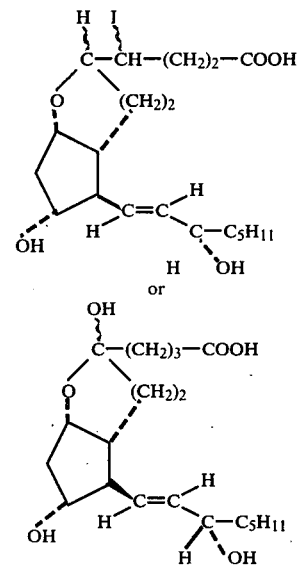

or a 4,5-didehydro feature, for example in an enol ether of the formula

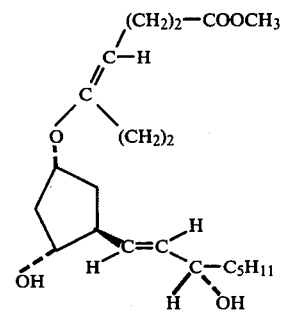

said derivatives having pharmacological activity. Processes for preparing them and the appropriate intermediates are disclosed.

15 Claims, No Drawings

PROSTAGLANDIN DERIVATIVES

CROSS REFERENCE TO RELATED APPLICATIONS

This application is a division of copending application Ser. No. 819,856 filed July 28, 1977 now issued as U.S. Pat. No. 4,123,441, which was a continuation-in-part of then copending application Ser. No. 725,546 filed Sept. 22, 1976, since abandoned, which was a continuation-in-part of then copending application Ser. No. 716,960 filed Aug. 23, 1976, since abandoned.

BACKGROUND OF THE INVENTION

This invention relates to prostaglandin derivatives and to a process for preparing them.

Some of the compounds of this invention may be regarded as analogs of prostacyclin and prostacyclin-type compounds.

The essential material for this application, including the background of the invention, the disclosure of the invention, and the description of the preferred embodiments, including Preparations and Examples, is incorporated by reference from issued U.S. Pat. No. 4,123,441 under the provisions of M.P.E.P. 608.01(p).

SUMMARY OF THE INVENTION

It is the purpose of this invention to provide novel products having pharmacological activity. It is a further purpose to provide processes for preparing these products and their intermediates.

Accordingly, there is provided a compound of the formula:

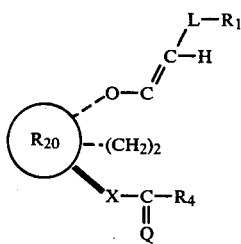

wherein $R_{20}$ is

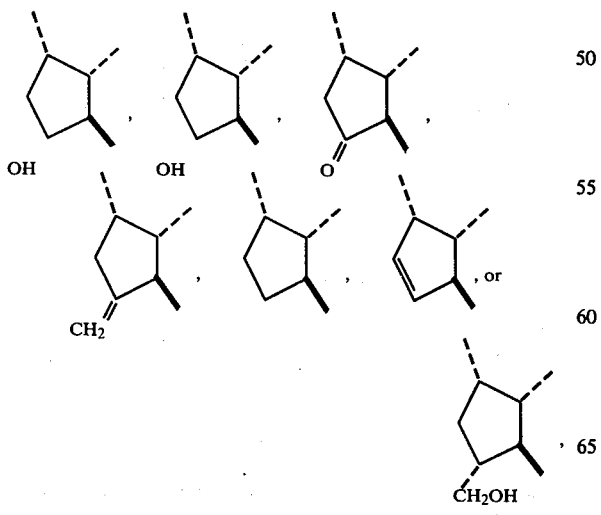

wherein L is
(1) $-(CH_2)_d-C(R_2)_2-$
(2) $-O-CH_2-Y-$ or
(3) $-CH|CH-$
   wherein d is zero to 5, $R_2$ is hydrogen, methyl, or fluoro, being the same or different with the proviso that one $R_2$ is not methyl when the other is fluoro, and Y is a valence bond, $-CH_2-$ or $-(CH_2)_2-$, wherein Q is

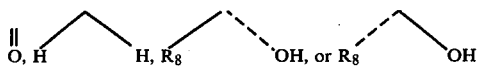

wherein $R_8$ is hydrogen or alkyl of one to 4 carbon atoms, inclusive, wherein $R_1$ is
(1) $-COOR_3$
(2) $-CH_2OH$
(3) $-CH_2N(R_9)(R_{18})$

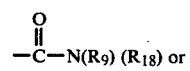

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

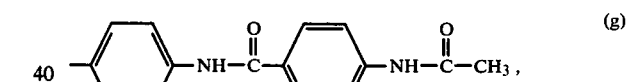

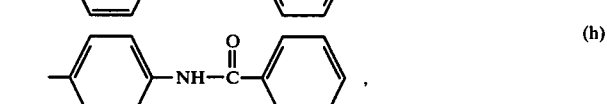

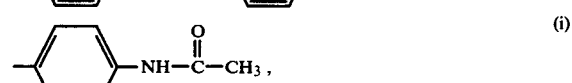

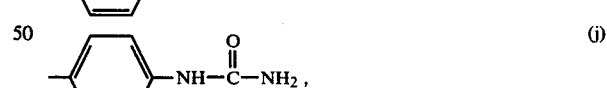

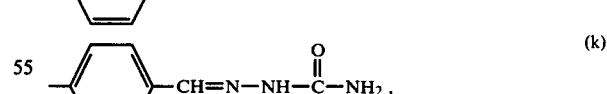

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_9$ is hydrogen, methyl, or ethyl, and $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein $R_4$ is

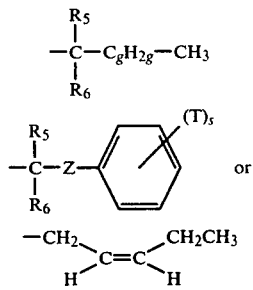

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring;

wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH=CH—
(2) cis—CH=CH—
(3) —C≡C— or
(4) —CH$_2$CH$_2$—;
including the lower alkanoates thereof.

In formula IV as used herein, attachment to $R_{20}$ corresponds to bonds to the cyclopentane ring at the C-8, C-9, and C-12 positions following prostaglandin nomenclature, thus:

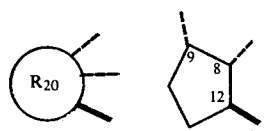

Within the scope of the prostaglandin derivatives described herein there are represented (a) PGF$_\alpha$ compounds when $R_{20}$ is

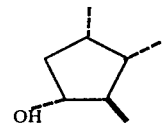

(b) 11β-PGF$_\alpha$ compounds when $R_{20}$ is

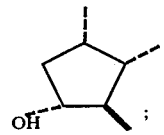

(c) 11-Deoxy-11-keto-PGF$_\alpha$ compounds when $R_{20}$ is

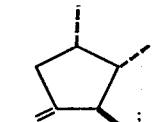

(d) 11-Deoxy-11-methylene-PGF$_\alpha$ compounds when $R_{20}$

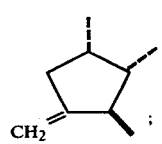

(e) 11-Deoxy-PGF$_\alpha$ compunds when $R_{20}$ is

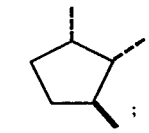

(f) 11-Deoxy-10,11-Didehydro-PGF$_\alpha$ compounds when $R_{20}$ is

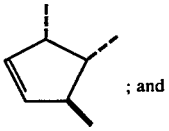; and (g) 11-Deoxy-11-hydroxymethyl-PGF$_\alpha$ compounds when $R_{20}$ is

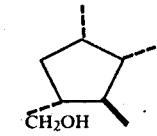

For those compounds of formula IV wherein Q is

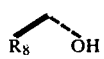

i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formula IV when Q is

and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

An example of the enol ethers of formula IV is represented by the formula

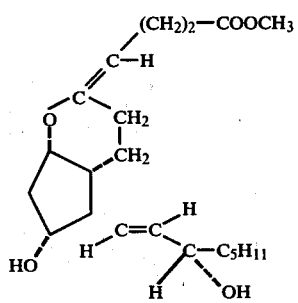

VIII named (4Z)-9-deoxy-5,9α-epoxy-Δ$^4$-PGF$_1$, methyl ester.

As to the "Z" and "E" nomenclature for stereoisomerism about a double bond, see for example J. E. Blackwood et al., J. Am. Chem. Soc. 90, 509 (1968).

I claim:

1. A 4Z compound of the formula

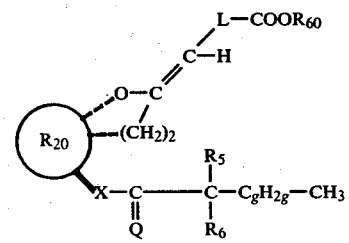

wherein R$_{20}$ is

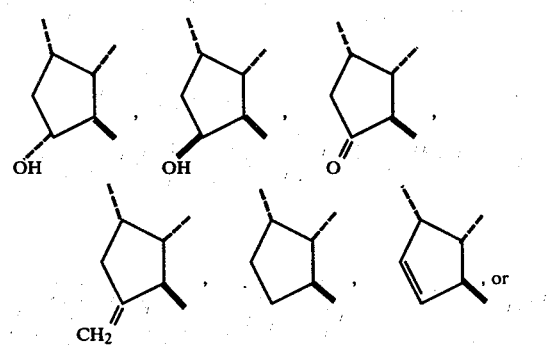

-continued

wherein L is —(CH$_2$)$_d$—C(R$_2$)$_2$—
  wherein d is zero to 5, R$_2$ is hydrogen, methyl, or fluoro, being the same or different with the proviso that one R$_2$ is not methyl when the other is fluoro,
wherein Q is

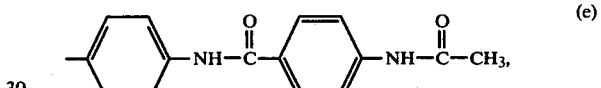

wherein R$_8$ is hydrogen or alkyl of one to 4 carbon atoms, inclusive.
wherein R$_{60}$ is (a) cycloalkyl of 3 to 10 carbon atoms, inclusive, (b) aralkyl of 7 to 12 carbon atoms, inclusive, (c) phenyl, (d) phenyl substituted with one, 2, or 3 chloro or alkyl of one to 4 carbon atoms, inclusive,

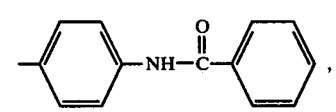
(e)

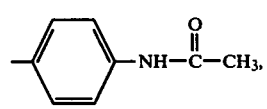
(f)

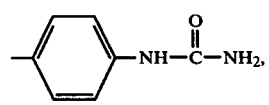
(g)

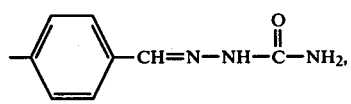
(h)

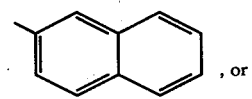
(i)

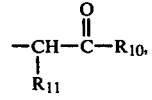
(j)

, or $$-\overset{|}{\underset{R_{11}}{C}}H-\overset{O}{\overset{\|}{C}}-R_{10},$$
(k)

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl,
wherein C$_g$H$_{2g}$ is alkylene of one to 9 carbon atoms, inclusive, with one to 5 carbon atoms, inclusive in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of $R_5$ and $R_6$ is fluoro only when the other is hydrogen or fluoro, and wherein X is
(1) trans—CH=CH—
(2) cis—CH=CH—
(3) —C≡C— or
(4) —CH$_2$CH$_2$—;

including the lower alkanoates thereof.

2. A 4E compound of the formula

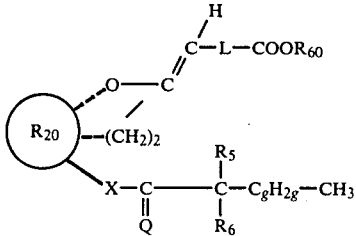

wherein $R_{20}$ is

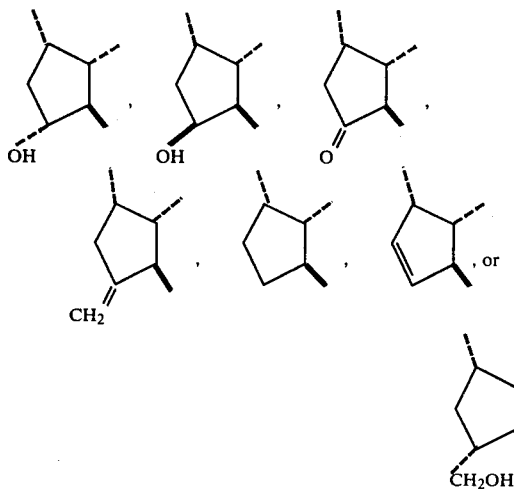

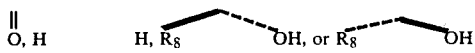

wherein L is —(CH$_2$)$_d$—C(R$_2$)$_2$—
wherein d is zero to 5, $R_2$ is hydrogen, methyl, or fluoro, being the same or different with the proviso that one $R_2$ is not methyl when the other is fluoro, wherein Q is

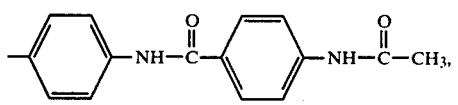

wherein $R_8$ is hydrogen or alkyl of one to 4 carbon atoms, inclusive.

wherein $R_{60}$ is (a) cycloalkyl of 3 to 10 carbon atoms, inclusive, (b) aralkyl of 7 to 12 carbon atoms, inclusive, (c) phenyl, (d) phenyl substituted with one, 2, or 3 chloro or alkyl of one to 4 carbon atoms, inclusive,

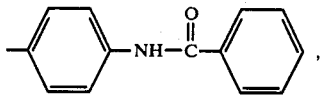 (e)

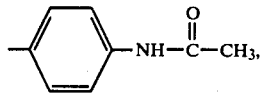 (f)

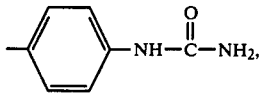 (g)

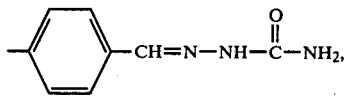 (h)

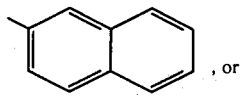 (i)

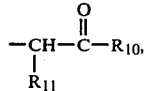 (j)

$$-\underset{R_{11}}{\underset{|}{CH}}-\overset{O}{\underset{\|}{C}}-R_{10},$$ (k)

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, wherein $C_gH_{2g}$ is alkylene to one to 9 carbon atoms, inclusive, with one to 5 carbon atoms, inclusive, in the chain between —CR$_5$R$_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro; and wherein X is
(1) trans—CH=CH—
(2) cis—CH=CH—
(3) —C≡C— or
(4) —CH$_2$CH$_2$—;

including the lower alkanoates thereof.

3. A compound according to claim 1 wherein $R_{20}$ is

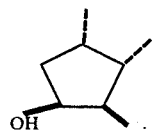

4. A compound according to claim 1 wherein $R_{20}$ is

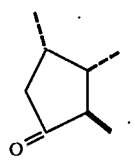

5. A compound according to claim 1 wherein $R_{20}$ is

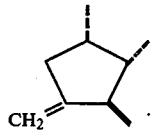

6. A compound according to claim 1 wherein $R_{20}$ is

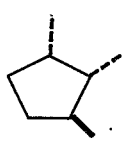

7. A compound according to claim 1 wherein $R_{20}$ is

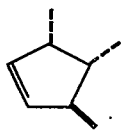

8. A compound according to claim 1 wherein $R_{20}$ is

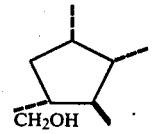

9. A compound according to claim 1 wherein $R_{20}$ is

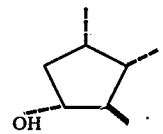

10. A compound according to claim 9 wherein L is —(CH$_2$)$_n$—, n being 2, 3, or 4, wherein Q is

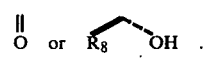

wherein R$_8$ is hydrogen, methyl, or ethyl, and wherein C(R$_5$)(R$_6$)—C$_g$H$_{2g}$—CH$_3$ is n-pentyl, 1,1-dimethylpentyl or 1,1-difluoropentyl.

11. A compound according to claim 10 wherein $R_{60}$ is

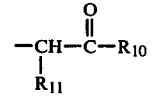

12. A compound according to claim 10 wherein X is —C≡C—.

13. A compound according to claim 10 wherein X is —CH$_2$CH$_2$—.

14. A compound according to claim 10 wherein X is trans-CH=CH—.

15. (4Z)-9-Deoxy-5,9α-epoxy-Δ$^4$-PGF$_1$, p-phenylphenacyl ester, a compound according to claim 11.

* * * * *

UNITED STATES PATENT OFFICE
CERTIFICATE OF CORRECTION

Patent No. 4,196,283         Dated  1 April 1980

Inventor(s)  Roy A. Johnson

It is certified that error appears in the above-identified patent and that said Letters Patent are hereby corrected as shown below:

In the title, "Prostaglandin Derivatives" should read -- Enlarged-Hetero-Ring Prostacyclin Analogs --;

In the abstract, line 1, "(PG$_1$ derivatives" should read -- (PG$_1$) derivatives --; that portion of the first formula reading

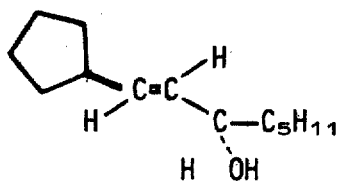 should read 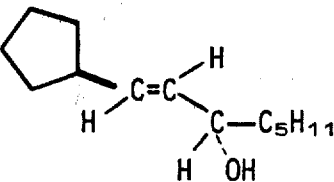 ;

that portion of the third formula reading

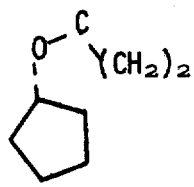 should read 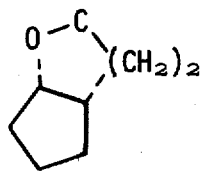 ;

Column 1, lines 35-45,

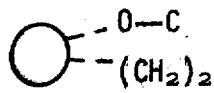 should read 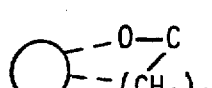 ;

Column 1, lines 47-54,

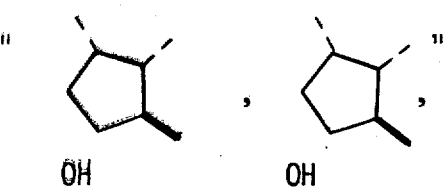 should read 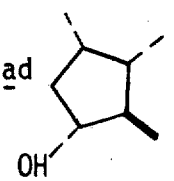 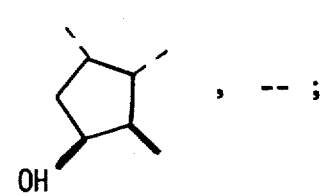 , -- ;

UNITED STATES PATENT OFFICE
CERTIFICATE OF CORRECTION

Patent No. 4,196,283      Dated 1 April 1980

Inventor(s) Roy A. Johnson

It is certified that error appears in the above-identified patent and that said Letters Patent are hereby corrected as shown below:

Column 2, line 4, "-CH|CH-" should read -- -CH=CH- --

Column 6, lines 15-19, "  " should read -- 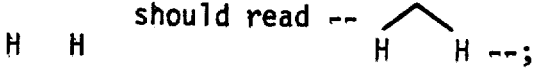 --;

Column 7, lines 51-55, " " should read -- --;

Column 10, line 35, the following should be added to claim 11:

-- wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl. --

*Signed and Sealed this*

*Twenty-fourth* Day of *March 1981*

[SEAL]

Attest:

RENE D. TEGTMEYER

*Attesting Officer*     *Acting Commissioner of Patents and Trademarks*